United States Patent
Karimian Azari et al.

(10) Patent No.: US 11,127,413 B2
(45) Date of Patent: Sep. 21, 2021

(54) AUDIO ALERT AUDIBILITY ESTIMATION METHOD AND SYSTEM

(71) Applicants: BlackBerry Limited, Waterloo (CA); 2236008 Ontario Inc., Waterloo (CA)

(72) Inventors: Sam Karimian Azari, Burnaby (CA); Mark Robert Every, Surrey (CA)

(73) Assignee: BlackBerry Limited, Waterloo (CA)

( * ) Notice: Subject to any disclaimer, the term of this patent is extended or adjusted under 35 U.S.C. 154(b) by 0 days.

(21) Appl. No.: 16/505,763

(22) Filed: Jul. 9, 2019

(65) Prior Publication Data
US 2021/0012788 A1    Jan. 14, 2021

(51) Int. Cl.
| G06F 17/00 | (2019.01) |
| G10L 21/0224 | (2013.01) |
| B60Q 5/00 | (2006.01) |
| G10L 21/0208 | (2013.01) |
| G10L 21/0216 | (2013.01) |

(52) U.S. Cl.
CPC .......... *G10L 21/0224* (2013.01); *B60Q 5/005* (2013.01); *G10L 2021/02087* (2013.01); *G10L 2021/02163* (2013.01)

(58) Field of Classification Search
CPC ....................................................... H03G 3/32
See application file for complete search history.

(56) References Cited

U.S. PATENT DOCUMENTS

| 2005/0195994 | A1* | 9/2005 | Saito | H03G 3/32 |
| | | | | 381/102 |
| 2006/0017561 | A1 | 11/2006 | Albert | |
| 2007/0239456 | A1 | 10/2007 | Goodman et al. | |
| 2008/0161063 | A1* | 7/2008 | Schuster | H04M 19/044 |
| | | | | 455/567 |
| 2009/0146799 | A1* | 6/2009 | Goldstein | B60Q 5/00 |
| | | | | 340/463 |
| 2011/0305346 | A1* | 12/2011 | Daubigny | H03G 3/32 |
| | | | | 381/28 |
| 2012/0123773 | A1* | 5/2012 | Zeng | G10L 21/0208 |
| | | | | 704/226 |
| 2016/0005308 | A1* | 1/2016 | Kohlrausch | G08B 3/10 |
| | | | | 381/57 |
| 2016/0283681 | A1 | 9/2016 | Falck et al. | |
| 2017/0039822 | A1* | 2/2017 | Schlesinger | G08B 3/10 |

FOREIGN PATENT DOCUMENTS

EP    2787746 A1    10/2014

OTHER PUBLICATIONS

EPO: Extended European Search Report relating to EP application No. 20176382.8, dated Oct. 28, 2020.

* cited by examiner

*Primary Examiner* — Joseph Saunders, Jr.
(74) *Attorney, Agent, or Firm* — Rowand LLP (57) ABSTRACT

A method and system of estimating human perception of audibility of audio alerts in the presence of background noise. In the audibility estimation system, a microphone generates an input signal corresponding to an audio alert. A processor receives the input signal and generates an audibility metric representing human perception of audibility of the audio alert based on a comparison between a background noise estimate and an audio alert estimate, and causes an action to be taken based on the audibility metric.

16 Claims, 4 Drawing Sheets

| SNR dB | Mean Opinion Score (Car Noise) | Audibility Metric (Car Noise) | Mean Opinion Score (Music) | Audibility Metric (Music) |
|---|---|---|---|---|
| 5 | 3.975 | 3.7678 | 3.75 | 3.4387 |
| 0 | 3.975 | 3.652 | 3.45 | 3.1495 |
| -5 | 3.675 | 3.4843 | 2.825 | 2.7649 |
| -10 | 3.225 | 3.247 | 2.45 | 2.3155 |
| -15 | 2.8 | 2.8921 | 1.925 | 1.8691 |
| -20 | 2.425 | 2.4238 | 1.45 | 1.441 |
| -25 | 1.95 | 1.8685 | 1.05 | 1.1584 |

AUDIO ALERT AUDIBILITY ESTIMATION METHOD AND SYSTEM

FIELD

The present application generally relates to human-machine systems for alerting humans, and more particularly, to methods and systems for estimating the audibility of audio alerts in such systems.

BACKGROUND

Audio alert generation systems are used to produce an audio alert to signal a particular state or condition to a human. An example of an audio alert is an audible tone, chirp, chime, voice message or other sound pattern. Such an audio alert generation system may be used to generate a number of different audio alerts on command from a variety of other systems or subsystems. For instance, an audio alert generation system in a vehicle may be configured to a generate audible alerts for a lane-departure warning system, a turn-signal system, a near-object (pedestrian or parking) detection system, an impending collision warning system, or any number of other such systems. These systems may be safety related, but are not always safety related. For example, some of these systems may be related to features that assist the vehicle operator, such as warnings for low fuel levels or enabled parking brakes.

The proper functioning and audibility of the audio alert generation system can be important, particularly if the audio alerts relate to safety warnings. Unfortunately, the audibility of audio alerts may be affected by background noise conditions. Examples of background noises in a vehicle include engine noise, tire noise, radio noise, passenger noise, ventilation noise, or any number of other such sounds.

It would be advantageous to provide for enhanced reliability and audibility of an audio alert generation system.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

In a first aspect, the present application describes a method of estimating human perception of the audibility of an audio alert in the presence of a background noise. The method includes obtaining an input signal from a microphone, obtaining a reference signal corresponding to the audio alert, obtaining from the input signal and the reference signal a background noise estimate and audio alert estimate represented at the microphone, generating an audibility metric representing human perception of audibility of the audio alert based on a comparison between the background noise estimate and the audio alert estimate; and taking an action based on the audibility metric.

In another aspect, the present application describes an alert audibility estimation system for estimating human perception of the audibility of an audio alert in the presence of a background noise. The alert audibility estimation system may include a processor, a microphone for generating an input signal corresponding to the audio alert and the background noise, and a memory storing processor executable instructions that, when executed by the processor, cause the processor to receive an audio input signal from a microphone, receive a reference signal corresponding to the audio alert, obtain from the audio input signal and the reference signal a background noise estimate and audio alert estimate represented at the microphone, generate an audibility metric representing human perception of the audibility of the audio alert based on a comparison between the background noise estimate and the audio alert estimate, and cause an action to be taken based on the audibility metric.

In yet a further aspect, the present application describes non-transitory computer-readable storage medium storing processor-readable instructions that, when executed, configure a processor to perform one or more of the methods described herein. In this respect, the term processor is intended to include all types of processing circuits or chips capable of executing program instructions.

Other aspects and features of the present application will be understood by those of ordinary skill in the art from a review of the following description of examples in conjunction with the accompanying figures.

In the present application, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

The present application relates to human-machine interfaces designed to signal an audio alert or audio alarm to a human. The terms "alert" and "alarm" are used interchangeably in the description below and are generally intend to be sensible signals to a human user or occupant, typically used to attract the human's attention to a current state of the machine. In many situations, the audio alert or audio alarm may be a warning to the human.

Alert generation finds particular application in human-machine environments such as vehicles. Vehicles have developed a specific hardware-software subsystem for generating audible alerts using a dedicated electronic control unit (ECU), typically referred to as the "chime generator" ECU.

Figure 1:
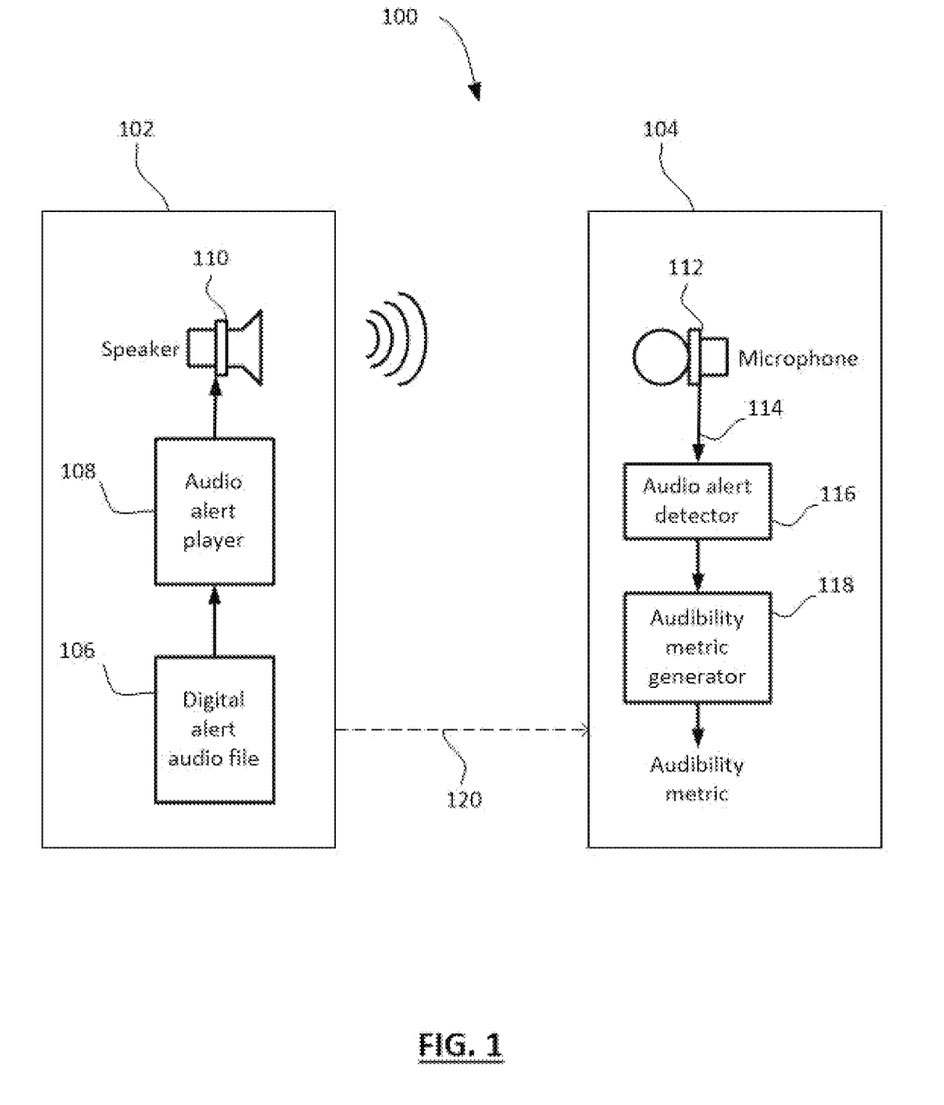
FIG. 1 shows an example of a simplified system for estimating human perception of the audibility of an audio alert in an alert generation system.

FIG. 1 shows, in block diagram form, a simplified example of one system 100 for estimating the audibility of an audio alert generated by an alert generation system 102. The alert generation system 102 generates an audible alert to be heard by a human. The alert generation system 102 includes an audio alert player 108 that, generally, selects a stored digital audio file 106 for the type of alert to be output. The audio alert player 108 converts the stored digital audio file 106 to an analog audio signal which is used to drive a speaker 110. In this manner, the alert represented by the stored digital alert audio file 106 is output as acoustic data from the speaker 110.

Audio alert player 108 includes a mix of software and hardware components. It will be appreciated that the software aspects of the player 108 may be implemented by way of processor-executable instructions executed by one or more processors. The processors may include a microprocessor and memory storing the instructions, a microcontroller, an application-specific integrated chip (ASIC), or any other such computing structure. The hardware components may include a digital to audio converter and an amplifier.

The stored digital alert audio file 106 may be in compressed or uncompressed format. In one example, the stored digital alert audio file 106 is a WAV file, although other audio file types may be used in other embodiments.

The stored digital alert audio file 106 may contain one or more audio channels or tracks of audio content. Typically, each audio channel in the stored digital alert audio file 106 corresponds to a speaker 100, or a group of speakers 110, in the alert generation system 102. Accordingly, the audio alert player 108 may output each channel in the stored digital alert audio file 106 through a corresponding speaker 110. In some embodiments, the alert generation system 102 may be a system that supports playback of only two channels on separate left and right speakers 110, in which case it may be referred to as a stereo audio system. In some other embodiments, the alert generation system 102 may be configured to support playback of more than two channels, in which case it may be referred to as a multi-channel playback system or a surround sound system.

The playback chain described above functions to output alarms or alerts to a human, such as a driver in the case of a vehicle. These alerts and alarms may provide critical information to the human. For example, the alert or alarm may signal an imminent danger detected by the vehicle's pedestrian-detection system, parking assist system, on-board diagnostic system, or any other such system. It will be noted that the audibility of the alerts and alarms may be affected by background noise conditions. For example, background noises in a vehicle such as engine noise, tire noise, ventilation noise, or any other such sounds may impair the ability of the human/driver to hear alerts and alarms. Failure to hear the output of the alert system could have serious consequences.

The present application describes an alert audibility estimation subsystem (AAES) that monitors the audio alert generation system with a view to verifying that playback has occurred and providing a perceptual audibility metric that corresponds to the audibility of the alert. In general, the AAES compares the expected output of the audio alert generation system with the signal received at a microphone and generates an audibility metric representing an estimation of human perception of audibility of the audio alert. An audibility metric that fails to meet a certain threshold may indicate that the alert was inaudible. An indication of the inaudibility of the alert can be provided through another (fallback) alert system to alert the human/driver.

The system 100 shown in FIG. 1 includes an alert audibility estimation system 104. The alert audibility estimation system 104 obtains the reference data 120 for the audio alert from the alert generation system 102. The reference data 120 may include, for example, the stored digital alert audio file 106 for the particular alert. In some embodiments, the reference data 120 may also contain continuous multi-channel audio data. In this case, the alert generation system 102 may generate a continuous signal, having no predefined start or end point, and may transmit the continuous signal to the alert audibility estimation system 104 as a real-time stream. The real-time stream may contain multi-channel audio data that corresponds to the audio alert as it is being played and output from the speaker 110. In some other cases, the alert audibility estimation system 104 has obtained the reference data 120 in advance for all possible alert types. A reference audio alert signal may be obtained from the reference data 120.

The alert audibility estimation system 104 includes a microphone 112. Persons of skill in the art will appreciate that there can be one or more microphones 112 in the system. The microphone 112 captures the acoustic signal produced by the speaker 110 playing the audio alert, as well as background noise, and produces a corresponding electrical signal referred to as the input signal 114. The alert audibility estimation system 104 may include a converter (not shown) for processing the electrical signal and putting it into the same form and format as the reference data 120. The converter may include amplifying, filtering, digital-to-analog (DAC) conversion, and coding using an applicable CODEC corresponding to the reference data 120.

Once the input signal 114 is in the same digital format as the reference data 120, an audio alert detector 116 detects whether the audio alert forms part of the input signal 114. In doing so, the audio alert detector 116 divides or segments the input signal into a plurality of chunks or frames and classifies each individual frame into one four categories: inactive, detected, failure, and high noise. The inactive category denotes a condition where no audio alert is played, for instance, when the energy of a related frame of a reference audio alert signal is lower than a certain threshold. The reference audio alert signal corresponds to the stored digital audio file 106 provided as reference data 120. The detected category denotes a condition where an audio alert was played by the alert generation system 102 and the audio alert forms part of the input signal 114 frame. Audio alert detection is generally based on the extent to which the level of the audio alert exceeds the level of the background noise. The failure category denotes a condition where an audio alert was played, but the audio alert does not form part of the input signal 114 frame. Lastly, a high noise category denotes that the level of background noise is too high to accurately determine whether the audio alert forms part of the input signal 114 frame. The audio alert detector 116 outputs the classification results.

The audio alert detector 116 may also output other error information or diagnostics. For example, in some implementations, the audio alert detector 116 may use buffers to store copies of the input signal 114. Error information related to the occurrence of buffer underruns or overruns may be output by the audio alert detector 116.

The audio alert detector 116 may also generate and output an audio alert detection status. The audio alert detection status may be one of either inactive, detected, failure, or high noise, and may correspond to the categories noted above. The audio alert detection status is generally based on the classification results. Any number of suitable techniques for determining the audio alert detection status are contemplated by the present application. For example, the status may be based on a comparison of the classification results to a threshold. In some implementations, the failure status is assigned when the percentage of failure classifications is greater than a threshold. In some other implementations, the failure status is assigned when the ratio of failure classifications to detected classifications is greater than a threshold. In some other implementations, the failure status is assigned based on a statistical analysis of the classification results and the likelihood of failure of the alert generation system 102. The inactive, detected and high noise statuses may be assigned using similar techniques.

The alert audibility estimation system 104 may store data that is output by the audio alert detector 116 for further analysis or future query. The stored data may also include temporal markers and may be queried to determine the last time a failure was detected. In some implementations, further analysis is performed on the stored data to determine the likelihood of failure of the alert generation system 102. The likelihood of the failure can be used to improve decision making on uncertainties and oscillations in data, and support the trade-off between a false alarm, where the audio alert detector 116 erroneously detects no audio alert, and a false rejection, when the audio alert detector 116 erroneously detects an audio alert even though the alert generation system 102 fails to output the audio alert.

In some embodiments, the alert audibility estimation system 104 may provide a detection notification. The notification may provide an indication of the audio alert detection status or any other output of the audio alert detector 116, or cause an action to be taken. By way of non-limiting example, the indication may denote that the audio alert was either inactive, detected, failed to be detected or that the background noise was too high to allow for accurate detection. Any number of suitable techniques for triggering the audibility notification are contemplated by the present application. For example, the audibility notification may be provided based on the detection status being assigned a failure status.

The alert audibility estimation system 104 also includes an audibility metric generator 118 for generating an audibility metric that positively correlates with human perception of audibility of the audio alert. As with audio alert detection, the audibility metric is generally based on the extent to which the level of the audio alert exceeds the level of the background noise. The audibility metric is based a comparison between the estimated level of the audio alert signal that forms part of the input signal 114 and the estimated background noise signal that forms the input signal 114. More particularly, the audibility metric is based on the estimated signal to noise ratio in the input signal 114. The audibility metric is further based on a frequency-weighting that correlates with human perception of relative loudness.

In some implementations, the audibility metric is generated in response to the audio alert detector 116 classifying at least one frame of the input signal 114 as detected. In other implementations, the audibility metric is generated when the audio alert detection status is not failure. In some other implementations, the audibility metric is generated when there is a detection notification. In some other implementations, the audibility metric is generated independent of the output of the audio alert detector 116. Persons skilled in the art will appreciate that the audio alert detection status is typically not required to in order to generate the audibility metric. Accordingly, in some embodiments, the audio alert detector 116 and the audibility metric generator 118 may be configured in a serial arrangement as shown in FIG. 1, while in other embodiments they may be in a parallel arrangement (not shown). In some embodiments the audio alert detector 116 and the audibility metric generator 118 may be configured to pass information between each other.

In some embodiments, the alert audibility estimation system 104 may provide an audibility notification. The notification may provide the audibility metric or an indication of a classification of the audibility metric, or cause an action to be taken. By way of non-limiting example, the indication may denote that the audio alert is either inaudible, barely audible, audible, or clearly audible. Any number of suitable techniques for triggering the audibility notification are contemplated by the present application. For example, the audibility notification may be provided based on a comparison between the audibility metric and a threshold. In some implementations, the audibility notification is provided when the audibility metric is below a predetermined threshold.

In some cases, the audibility notification or detection notification is an interrupt or similar signal to another system for signaling the audibility of the audio alert. The interrupt may cause a fault condition in the other system, such as illumination of a warning light or a similar indicator of a fault. In some cases, the audibility notification may cause a message to be transmitted to an associated device, such as a mobile number or a smartphone application associated with the vehicle or to a third party system. The audibility notification or detection notification may be conveyed to a user, a service department or more than one entity.

In some cases, the audibility notification or detection notification may trigger a visual or haptic alert feedback system that serves as an alternative alert system to the audio alert generation system 102 to provide feedback to a user. For example, a haptic alert system may induce a vibratory alert or pattern into a steering wheel, driver's seat, or other object that the human may be expected to contact or be in close proximity to.

Other actions may also be triggered in response to the result of the comparison between the audibility metric and a threshold. An audibility metric that falls below a threshold may cause the alert generation system 102 to replay the audio alert. Similarly, an audio alert detection status of failure may also cause replay of the audio alert.

The audibility metric or audio alert detection status may also be used for tuning the alert generation system 102 and as feedback to make adjustments to alert generation system 102 metrics and the audio playback path in the alert generation system 102. For example, adjustments may be made to volume settings in order to increase the volume level of audio alerts output through the speaker 110. The output volume of the audio alert at the speaker 110 may be adjusted such that the audibility metric reaches a threshold value. Other actions that may be taken include determining a gain value to apply to the audio alert to adjust the signal-to-noise ratio of the input signal to a threshold level. Another action that may be taken is to modify one or more properties of the audio alert, such as pitch, and repeat playback.

In some cases, the audibility metric or audio alert detection status may cause another system or device that outputs sound from the speaker 110, or any other speaker, to be turned off, muted or have its volume level decreased. An example of such a device includes a car radio. In some cases, the audibility metric may cause sounds other than the audio alert to be blocked from being output from the speaker 110 or other speakers, or cause the output volume of those other sounds to be lowered to a level which will allow a replay of the audio alert or a subsequent audio alert to reach a suitable level of audibility.

In some embodiments, a simulation may be conducted prior to playing the audio alert. The simulation may generate a predicted or simulated audibility metric based on the input signal 114 prior to playing the audio alert. The predicted audibility metric may be based on the acoustic power of the background noise obtained from the input signal 114 prior to playing the audio alert. Any number of actions may be taken based on the predicted audibility metric, including actions that may be taken in response to an audibility metric based on actual playback of the audio alert. In some cases, the output volume of the audio alert at the speaker 110 may be adjusted such that the simulated audibility metric reaches a threshold value. In other some cases, the alert generation system 102 may have a plurality of stored digital audio files 106 corresponding to a particular type of audio alert. The plurality of stored digital audio files 106 may include different versions of the audio alert. Some versions of the audio alert may be more audible than others for a particular background noise condition. The simulation may select the version of the audio alert having the highest simulated audibility metric for the background noise condition.

In some embodiments, the acoustic power of the background noise may be obtained from the input signal 114 prior to the alert generation system 102 outputting the audio alert. The volume of the audio alert may be increased if the acoustic power is above a threshold value.

Different notification, alerting and warning techniques known in the art may be used to convey the output of the alert audibility estimation system 104, the audio alert detector 116 and the audibility metric generator 118. In the embodiments described above, the system may also include a wired or wireless transmitter (not shown). The alert audibility estimation system 104 may communicate output using a transmitter, a message or a notification to the driver of the vehicle and/or to a third party based on the results obtained. By way of non-limiting example, a third party may be a service department and the message may provide that the vehicle is in need of a check-up or repair. The message may include the input signal 114 in a format familiar to a technician or mechanic so that it may be used directly for making a diagnosis. The message may also include information about the vehicle and the type of audio alert.

It will be appreciated that portions of the alert audibility estimation system 104 may be implemented by way of software, i.e. processor-executable instructions that, when executed by one or more processors, cause the processors to carry out the described operations. For example, the processing of the input signal 114 in the audio alert detector 116 and in the audibility metric generator 118 may be implemented by way of software instructions. That is, a suitably programmed processor may implement the digital signal processing for detecting the audio alert and generating an audibility metric. These software-implemented operations may be described herein as an alert audibility estimation module, but the term "module" is not intended to imply any particular programming language or structure and may be used interchangeably with application, component, program, or the like. The alert audibility estimation module may be implemented, in some cases, as an application-specific integrated circuit or the like.

Persons ordinarily skilled in the art will appreciate that in some embodiments the alert generation system 102 and the alert audibility estimation system 104 share one or more processors. System 100 can play an audio alert at the speaker 110 and immediately look for a corresponding acoustic signal at the microphone 112 in order to detect the playing of the audio alert and generate the audibility metric.

Figure 2:
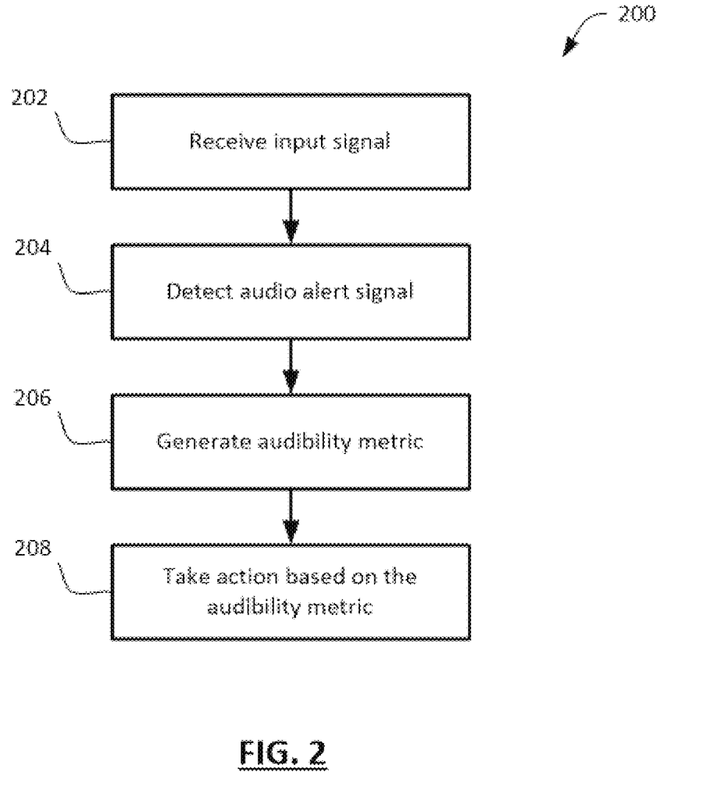
FIG. 2 shows a flowchart illustrating an example method of estimating human perception of the audibility of an audio alert in the presence of a background noise.

Reference is now made to FIG. 2, which shows, in flowchart form, a simplified example of a method 200 of estimating human perception of the audibility of an audio alert in the presence of a background noise. It will be appreciated that the method 200 occurs substantially in an alert audibility estimation system.

The method 200 includes receiving an input signal from a microphone in operation 202. The input signal $y_m(n)$ at the mth microphone can be represented as a mixture of an audio alert reference signal $s_d(n)$ from the dth speaker and a background noise signal $v_m(n)$ at the mth microphone as follows:

$$y_m(n) = s_d(n) * h_{d,m}(n) + v_m(n) \quad (1)$$

where n denotes a discrete-time index, $h_{d,m}(n)$ is the impulse response of the acoustic path from the dth speaker to the mth microphone, and * denotes the convolution operation. Accordingly, $s_d(n) * h_{d,m}(n)$ is the acoustic signal, sometimes referred to as the echo, on the mth microphone in response to the audio alert reference signal $s_d(n)$ played from the dth speaker.

The system can predict and detect multiple audio alerts individually, or the combination of a group of the audio alerts output from all of the speakers. For example, the relationship between the audio alert signal at the mth microphone, represented by $x_m(n)$, and the audio alert signals output from all of the speakers, is given by:

$$x_m(n) = \sum_{d=1}^{D} s_d(n) * h_{d,m}(n) \quad (2)$$

where D is the total number of speakers. It is noted that the audio alert signal $x_m(n)$ is based on one or more reference signals and is sometimes referred to as the actual audio alert signal at the mth microphone.

Many of the embodiments described herein focus on the detection and audibility of a single audio alert output from a group of the speakers in an alert generation system. However, it is understood that the present application is not limited to such embodiments and that the embodiments described generally can easily be extended to detect audio alerts and generate audibility metrics and other outputs for individual audio alerts.

Signal processing algorithms are used to process the input signal. The digitized input signal is divided into chunks or frames. The frames may overlap each other. It is understood that the length of each frame should be larger than the maximum delay between the speakers and the microphones.

A window may be applied to each frame to produce a smooth estimate of the resulting complex spectrum. Any number of techniques for implementing a suitable smoothing window may be used, including a Hann or Hamming function.

A discrete Fourier transform (DFT) is applied to each windowed frame to obtain the complex spectrum that separates the signal into frequency bins. The complex spectrum is divided into K contiguous frequency bins. Each bin is identified across a small frequency band. In some implementations, the bins cover only the audible frequency range at which humans can hear. In some other implementations, the complex spectrum is divided into octave bands, where an octave band is commonly defined as a band bounded by an upper frequency and a lower frequency where the upper frequency is twice the lower frequency. Octave bands may result in a relatively coarse distribution and therefore some implementations may use fractional octave bands instead, for example, one third (⅓) octave bands.

The mixture of the audio alerts and noise is represented at frequency bin index k and frame index q as:

$$Y_m(k,q) = X_m(k,q) + V_m(k,q) \qquad (3)$$

where $Y_m(k,q)$ is the input signal at the mth microphone, $X_m(k,q)$ is the audio alert signal at the mth microphone, and $V_m(k,q)$ is the background noise signal at the mth microphone. In implementations using octave bands, the frequency bin index k is understood to refer to an octave band index or a fractional octave band index.

Each bin identifies a magnitude spectrum and may be converted into the power-spectral domain to estimate the power spectral density (PSD). The additive noise is assumed to be zero mean and uncorrelated with the mixture of the audio alerts. Therefore, the expected PSD of the input signal has the form:

$$E|Y_m(k,q)|^2 = E|X_m(k,q)|^2 + E|V_m(k,q)|^2 \qquad (4)$$

where $E|\cdot|$ denotes the mathematical expectation of the magnitude spectrum. The expectations are obtained by removing high frequency components on the envelope of the magnitude spectrum. This can be accomplished via the windowing techniques noted above. In some embodiments, the expected PSD also includes frequency dependent smoothing, for example, fractional octave band smoothing.

Referring again to FIG. 2, operation 204 involves detecting in the input signal an audio alert signal related to the audio alert. Some of the algorithms for detecting whether the audio alert signal forms part of the input signal rely on obtaining an estimated background noise signal $\hat{V}_m(k,q)$ from the input signal.

In some embodiments, the estimated background noise signal is obtained while the audio alert is inactive. An audio alert may be considered inactive when it is not being output at the dth speaker or when the frame energy of the reference audio alert signal is less than a threshold digital value. The system 104 can also include a power detector (not shown) for averaging the acoustic power in each input signal frequency bin during the periods when the audio alert is not active. The estimated background noise signal is the input signal at the mth microphone during a selected period of audio alert inactivity.

In some implementations, the selected period of inactivity is an earlier period of inactivity immediately prior to the audio alert becoming active. In other implementations, the selected period is a later period of inactivity immediately following the active audio alert, where the audio alert is no longer active. In yet other implementations, it is a combination of the earlier and later periods of inactivity. In yet other implementations, the selection of the period of inactivity is made on the basis of a comparison between two periods of inactivity. For example, comparing the average acoustic power of an earlier period of inactivity to the average acoustic power of a later period of inactivity, and selecting between the compared periods the period of inactivity having the greater average acoustic power. In other implementations, the estimated background noise signal may be obtained using minimum statistics tracking or leaky integrators on the magnitude spectra of the microphone input signal and may include slew rate constraints on upwards and downwards ramping speed of the estimated background noise signal.

In some other embodiments, the estimated background noise signal is obtained from an input signal containing the active audio alert. In such embodiments, the estimated background noise signal may be obtained based on the audio alert reference signal, and by estimating acoustic path information from the speaker to the microphone, such as the impulse response of the acoustic path, in real time. In one example, the estimated background noise signal is obtained using an adaptive filtering approach. An adaptive gain filter, $w_{d,m}(n)$, is applied to the dth audio alert reference signal, $s_d$, to obtain a prediction of the audio alert signal, $\tilde{x}_m(n)$, received at the mth microphone, as given by:

$$\tilde{x}_m(n) = \sum_{d=1}^{D} \sum_{i=0}^{N} w_{d,m}(i) s_d(n-i) \qquad (5)$$

where N is the length of the adaptive filter. It is understood that the length of the filter should be large enough to cover the information of the acoustic path. It is also understood that although the adaptive gain filter noted above is designed in the time domain, it may be implemented in the frequency domain by multiplication instead of convolution.

The adaptive filter may be applied using any one of a number of suitable adaptive algorithms, including but not limited to a least-mean-square (LMS) algorithm, a normalized LMS (NLMS) algorithm, an affine projection algorithm or a recursive least-square (RLS) algorithm.

The estimated background noise signal is a pseudo-error signal and is the difference between the input signal and the predicted audio alert signal. Thus the estimated background noise signal is obtained by subtracting the predicted audio alert signal from the input signal and can be calculated as follows:

$$\hat{v}_m(n) = y_m(n) - \tilde{x}_m(n) \qquad (6)$$

Some of the algorithms for detecting the audio alert signal also rely on obtaining estimated acoustic path information between each of the speakers and each of the microphones. Accordingly, the impulse response or transfer function of the acoustic path may be measured or estimated.

Generally, the acoustic path information may be obtained through a prior calibration of the system 100 that measures the acoustic coupling between the audio alert reference signal at the speaker 110 and the audio alert signal at the microphone 112. Any variable gains in the playback path in the alert generations system, for example, a volume control on an external amplifier, should be known at all times, otherwise the audio alert detector may not function properly.

The prior calibration includes estimating the acoustic path information between each of the speakers and each of the microphones. This may include outputting a test calibration signal, for example, a controlled sweep signal or a random noise signal, from each speaker of the alert generation system and measuring or estimating the response at each microphone. This prior acoustic path information may be stored in a location accessible to the alert audibility estimation system.

The prior acoustic path information for the sound propagating between the particular locations of the speaker 110 and the microphone 112 is generally time-invariant in a static acoustic environment. However, the acoustic environment may change depending on, for example, air pressure, temperature and humidity. Accordingly, in cases where the system 100 is online after production, for example when a vehicle is being driven, the prior acoustic path information may not accurately reflect the online acoustic environment. In such a scenario, outputting a test calibration signal to update the acoustic path information may not be suitable, as it may distract or annoy the driver or other occupants of the vehicle. Ideally, the acoustic path information is updated without the driver realizing that the system 100 is being calibrated.

In cases where the acoustic paths are time-varying to a significant degree, an online calibration method may use signals that are concurrently playing out of the speakers 110, such as radio, speech or music, to adapt the calibration estimates of the transfer functions, rather than by playing a test calibration signal, which may be objectionable to a vehicle's occupants. In some embodiments, the acoustic path information is estimated and updated using the adaptive filter $w_{d,m}(n)$ noted above during the time that the audio alert is detected by the audio alert detector 116.

The acoustic path information can be applied to predict the short term spectra of the incoming audio alerts. For example, the power spectrum of the predicted audio alert signal at the mth microphone may be given by:

$$E|\tilde{X}_m(k, q)|^2 = \sum_{d=1}^{D} E|S_d(k, q)|^2 E|\hat{H}_{d,m}(k)|^2 \tag{7}$$

where, $E|S_d(k,q)|^2$ is the power spectrum of the audio alert reference signal at the dth speaker, $E|\hat{H}_{d,m}(k)|^2$ is the power spectrum of the transfer function of the acoustic path between the dth speaker and the mth microphone.

As noted above, detecting the audio alert involves classifying individual frames of the input signal into one of four categories. The classification process may involve performing a comparison between the frame energy of the audio alert reference signal, $E|S_d(q)|^2$, and a predetermined threshold value. If the frame energy of the reference signal is lower than the threshold, the frame may be assigned a classification indicative of no audio alert being active. If the frame is not classified as inactive, the frame may be assigned a classification of either detected, failure or high noise, as the case may be.

If the frame is not classified as inactive, the system may perform a comparison to decide between assigning a classification of detected or a classification of failure. A cross correlation comparison based on the power spectrum of the predicted audio alert signal and the power spectrum of the estimated signal may be performed to determine whether the predicted audio alert signal is present in the input signal. The short-term cross correlation coefficient, $r_m(q)$, represented in the frequency domain, is given by:

$$r_m(q) = \frac{\sum_{k=0}^{K-1} E|\tilde{X}_m(k, q)| E|\hat{X}_m(k, q)|}{\sum_{k=0}^{K-1} E|\tilde{X}_m(k, q)|^2} \tag{8}$$

where $\tilde{X}_m$ is the predicted audio alert signal at the mth microphone and $\hat{X}_m$ is the estimated audio alert signal at the mth microphone and is sometimes referred to as the noise suppressed microphone signal. The audio alert may be estimated using a noise reduction algorithm with the primary goal of estimating the alert from the noisy input. Suitable algorithms include, but are not limited to, statistical-model-based (e.g., Wiener filter) or spectral-subtractive algorithms. For example, the estimated audio alert using the spectral-subtractive algorithm is given by:

$$E|\hat{X}_m(k,q)|^2 = E|Y_m(k,q)|^2 - E|\hat{V}_m(k,q)|^2 \tag{9}$$

where $Y_m$ is the input signal at the mth microphone and $\hat{V}_m$ is the estimated background noise signal at the mth microphone.

A correlation coefficient of 0.0 indicates the input signal $y_m(n)$ is uncorrelated to the predicted signal $\tilde{x}_m(n)$ and is indicative of the audio alert not being detected in the input signal. On the other hand, a correlation coefficient of 1.0 indicates a perfect positive relationship and is indicative of the audio alert being detected in the input signal without the presence of background noise in the input signal.

The correlation coefficient is compared to a predetermined threshold value. If the result of the correlation is lower than the threshold, then the frame may be assigned a classification indicative of either a failure to detect the audio alert or indicative of a high noise condition. Otherwise, the frame is assigned a classification indicative of a detection of the audio alert. The predetermined threshold values may vary from one audio alert signal to another and may vary for the same signal based on the vehicle and/or environmental parameters and characteristics known in the art.

In noisy environments, the short-term cross correlation coefficient may not yield an accurate result. Therefore, in some embodiments, the system may determine whether there is a high level of background noise. This determination is made based on the level of the pseudo signal-to-noise ratio (PSNR). The PSNR is defined as the ratio of the spectra-temporal of the reference audio alert to the noise and represented in dB as:

$$PSNR_m(q) = 20\log_{10} \frac{\sum_{k=0}^{K-1} E|\tilde{X}_m(k, q)|^2}{\sum_{k=0}^{K-1} E|\tilde{X}_m(k, q)| E|\hat{V}_m(k, q)|} \tag{10}$$

This ratio is biased towards looking at the frequency bins where the audio alert is expected to be. The ratio is compared to a threshold. If the ratio is below the threshold, the frame is classified as high noise. Otherwise, the frame is assigned the result of the short-term cross correlation comparison described above.

Referring again to FIG. 2, operation 206 involves generating an audibility metric correlated with human perception of audibility of the audio alert. The audibility metric is based on an analysis of the characteristics of the background noise and the input signal. The algorithm is a function of a time-frequency dependent measurement and compares the temporal envelopes of the magnitude spectrum of the estimated audio alert signal and the input signal in short-time regions by means of a correlation coefficient. The short-term correlation coefficient is defined as:

$$d_m(k, q) = \frac{E|Y_m(k, q)\hat{X}_m^*(k, q)|}{\sqrt{E|Y_m(k, q)|^2 E|X_m(k, q)|^2}} \tag{11}$$

where $Y_m$ represents the input signal, $X_m$ and $\hat{X}_m$ represent, respectively, the actual and the estimated audio alert signals at the mth microphone, and the asterisk denotes complex conjugation.

Since the audio alert and background noise are uncorrelated, equation 11 can be rewritten as:

$$d_m(k, q) = \frac{E|\hat{X}_m(k, q)|}{E|Y_m(k, q)|} \quad (12)$$

Equation 12 can be rewritten in terms of the signal-to-noise ratio (SNR) as follows:

$$d_m(k, q) = \sqrt{\frac{SNR_m(k, q)}{1 + SNR_m(k, q)}} \quad (13)$$

where $SNR_m(k,q)$ is the SNR in frequency bin index k and frame index q at the mth microphone. The SNR is the signal-to-noise ratio of the estimated audio alert signal $\hat{X}_m$ to the estimated background noise signal $\hat{V}_m$. Hence, the frequency bins which have positive SNR in dB are more likely to contribute to the audibility metric while bins with unfavorable SNR do not contribute significantly to the audibility metric. It is noted that the short-term correlation coefficient $d_m(k,q)$ has values between 0.0 and 1.0.

Equation 13 is applied to the active frequency bins/bands. For the purposes of equation 13, a frequency bin/band is considered active where the bin/band energy of the predicted audio alert signal at the mth microphone, $\hat{X}_m$, exceeds a threshold. The threshold may vary over time and may be computed as a fixed value in dB below the maximum across frequency bins of the predicted alert magnitude spectrum $\hat{X}_m(k,q)$.

The overall contribution of the calculations across all active frequency bins/bands, Q, may be defined as follows:

$$AM_m(q) = \sqrt{\sum_{k \in Q} \alpha(k) d_m^2(k, q)} \quad (14)$$

where $\alpha(k)$ is a normalized frequency-weighting over the active bands and $AM_m(q)$ represents the audibility metric at the mth microphone.

A frequency-weighting is considered normalized when the sum of the values in the frequency-weighting total one, which can be expressed mathematically as:

$$\sum_{k \in Q} \alpha(k) = 1 \quad (15)$$

One example of a frequency-weighting is A-weighting, which is defined in the international standard IEC 61672 (International Electrotechnical Convention). A-weight correlates with human judgments of relative loudness, and corresponds to the fact that the human ear is not as sensitive to sound of the lower frequencies. It is understood that other frequency weighting curves may be used instead of an A-weight.

In some embodiments, the audibility metric may be generated without applying a frequency-weighting to the short-term correlation coefficient or by applying an equally-weighted frequency-weighting. The alert audibility estimation system may instead attenuate certain frequencies in the input signal. For example, a high pass filter may be applied by the microphone to filter out low frequencies from the input signal. Any number of suitable techniques for attenuating or removing undesirable frequencies from the input signal are contemplated by the present invention.

Since the short-term correlation coefficient $d_m(k,q)$ has values between 0.0 and 1.0, the audibility metric also ranges between 0.0 (for inaudible) and 1.0 (for clearly audible). In some implementations, the audibility metric is mapped to audibility categories based on the range the metric falls within. For example, values between 0 and 0.25 might be classified as inaudible, 0.25 to 0.50 as barely audible, 0.50 to 0.75 as audible and 0.75 to 1.0 as clearly audible.

An audibility metric is generally generated for each input signal frame. An overall audibility metric can be generated for the audio alert by smoothing a time series of generated audibility metrics over time. In some implementations, an overall audibility metric is generated for the audio alert by taking an average of the audibility metrics generated for the input signal frames relating to the audio alert.

Referring again to FIG. 2, operation 208 involves taking an action based on the audibility metric. As noted above, any number suitable actions and notifications may be taken in response to the generation of the audibility metric.

Figure 3:
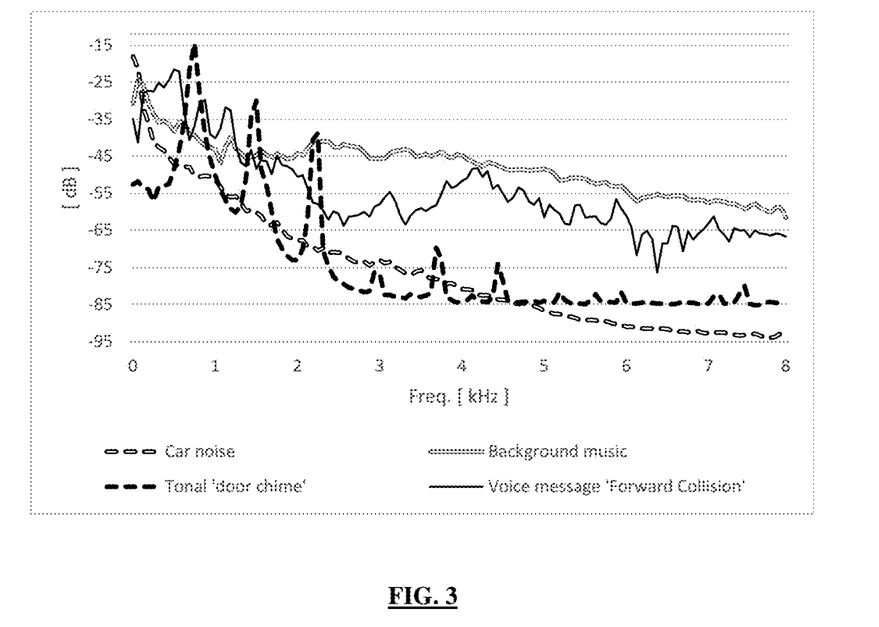
FIG. 3 shows examples of the relative average dB power spectrum of two noise conditions (car noise and background music) and two audio alerts (a tonal 'door audio alert' and a voice message 'forward collision')

FIG. 3 shows examples of the relative average dB power spectrum of two noise conditions (car noise and background music) and two audio alerts (a tonal 'door audio alert' and a voice message 'forward collision') for a vehicle. It is understood that the overall level of each sound may be adjusted up or down based on, for example, the vehicle's volume settings and speed.

Figure 4:
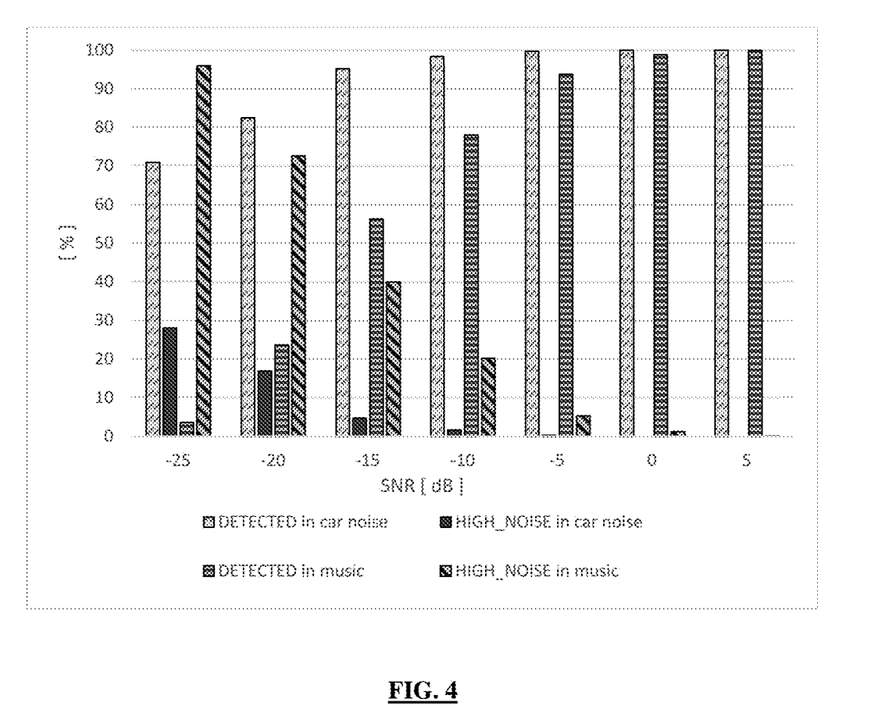
FIG. 4 shows experimental results from an experiment relating to the detection of audio alerts in the presence the two noise conditions of FIG. 3.

FIG. 4 shows experimental results from an experiment verifying the detection of audio alerts in the presence the two noise conditions of FIG. 3. The experiment involved playing four audio alerts separately in the presence of only one of the two noise conditions. The audio alerts were mixed with varying volumes of the two noise conditions, and the ratio of the power of the alert signal to the noise signal is shown as signal-to-noise ratio (SNR). The audio alerts included two tonal sounds and two voice messages, ten seconds in length and at the 16 kHz sampling frequency. The graph in FIG. 4 shows the percentage of frames that were classified in the "detected" and "high noise" categories. The car noise had dominant energy in the low frequency bands, whereas the background music covered all frequency bands of the audio alert in a low signal-to-noise ratio (SNR). Therefore, when the audio alerts were played in the presence of car noise, most of the frames were classified as "detected" irrespective of the SNR. On the other hand, when the audio alerts were played in the presence of background music, most of the frames were classified as "high noise" at low SNR.

Another experiment was conducted which demonstrates the positive correlation between the audibility estimation system and subjective responses. In the experiment, subjects experienced two different noise spectra in combination with the two different audio alerts, and provided ratings of their ability to hear the audio alerts with each noise condition. One audio alert was a tonal door audio alert and the other audio alert was a voice message consisting of a voice speaking the words "forward collision". The two noise conditions were car noise and background music. FIG. 3 shows the average magnitude spectrum of the car noise and background music, and the two audio alerts.

The experiment involved each of the two audio alerts separately in the presence of each of the two noise conditions. The SNR was an additional variable in the experiment. Opinion scores were obtained for seven different levels of SNR ranging from −25 dB to 5 dB. The audio alert and noise spectra were played from digital recordings. Each combination of audio alert and noise condition at a specified SNR was presented to the subjects, following which the subjects provided an audibility opinion score rating of their perception of the audibility of the audio alerts. The opinion scores were rated on a four-point audibility scale ranging from 1 to 4, with 1 denoting inaudible, 2 denoting barely audible, 3 denoting audible, and 4 denoting clearly audible.

The experiment also involved generating audibility metric measurements for the same audio clips (sets of audio alerts, noise conditions and SNR) applied in the subjective listening test. A non-linear function was applied to map the generated audibility metrics to a perceptual scale of audibility, namely the four-point audibility scale noted above. The mapped audibility metric values were determined by multiplying the audibility metric (AM) by three and adding one as follows:

$$\text{Mapped } AM_m(q) = AM_m(q) \times 3 + 1 \quad (16)$$

Figure 5:
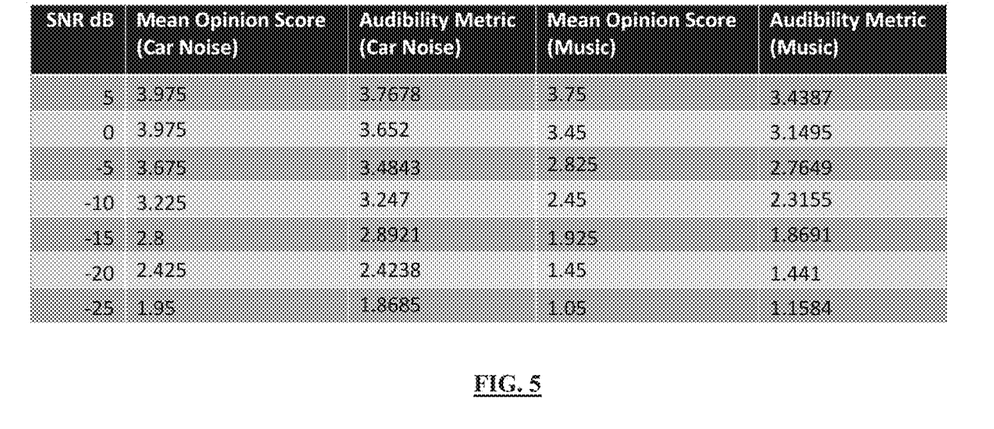
FIG. 5 shows experimental results, namely, mean opinion scores and acoustic metrics, from an experiment involving the noise conditions and audio alerts of FIG. 3.
Figure 6:
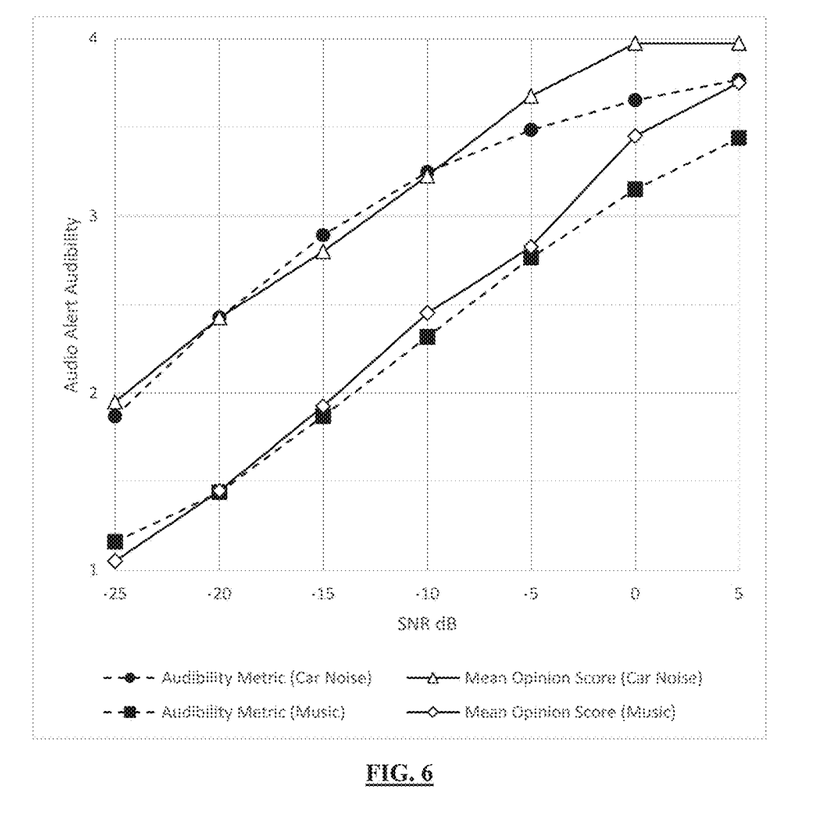
FIG. 6 shows the data of FIG. 5 in graphic form.

FIGS. 5 and 6 show the experimental results obtained from the subjective listening test compared with the corresponding generated audibility metrics. In FIG. 5, the mean opinion score from all participants for all audio alerts in the presence of the car noise condition is presented in the column labeled Mean Opinion Score (Car Noise). The corresponding mapped audibility metrics for the same audio alerts and noise condition are presented in the adjacent column labeled Mean Opinion Score (Car Noise). Similarly, the experimental results related to the background music noise condition are presented in the last two columns.

FIG. 6 shows the data of FIG. 5 in graphic form.

The experimental results show a close relationship between the acoustic metric generated by the audibility estimation system and actual human perception of the audibility of audio alerts in the presence of background noise. As shown in FIGS. 5 and 6, the audibility metric closely tracks the results of the subjective listening test. In particular, for the experimental data shown, the audibility metric is accurate to within approximately ten percent of human perception of the audibility of audio alerts.

The subject matter of the disclosure herein may also relate, among others, to the embodiments of the following clauses:

AA. A method of estimating human perception of the audibility of an audio alert in the presence of a background noise, the method comprising obtaining an input signal from a microphone, obtaining a reference signal corresponding to the audio alert, obtaining from the input signal and the reference signal a background noise estimate and audio alert estimate represented at the microphone, generating an audibility metric representing human perception of audibility of the audio alert based on a comparison between the background noise estimate and the audio alert estimate; and taking an action based on the audibility metric.

BB. The method of clause AA, wherein the comparison is a short-time cross correlation comparison.

CC. The method of clause AA or BB, wherein the comparison is based on a signal-to-noise ratio of the audio alert estimate to the background noise estimate.

DD. The method of any one of clauses AA to CC, wherein generating the audibility metric is further based on a frequency-weighting that correlates with human perception of relative loudness.

EE. The method of any one of clauses AA to DD, wherein obtaining the audio alert estimate is based on an impulse response of an acoustic path between a speaker and the microphone.

FF. The method of any one of clauses AA to EE, wherein obtaining the background noise estimate is based on adaptively filtering the audio alert from the input signal using the reference signal.

GG. The method of any one of clauses AA to FF, wherein obtaining the background noise estimate is based on a comparison between an acoustic power of the input signal when the audio alert is active and an acoustic power of the input signal when the audio alert is inactive.

HH. The method of any one of clauses AA to GG, wherein taking an action based on the audibility metric comprises playing the audio alert louder.

II. The method of any one of clauses AA to HH, wherein taking an action based on the audibility metric comprises modifying one or more properties of the audio alert and repeating playback.

JJ. The method of any one of clauses AA to II, wherein taking an action based on the audibility metric comprises providing visual or haptic feedback to a human.

KK. An alert audibility estimation system for estimating human perception of the audibility of an audio alert in the presence of a background noise, the system comprising a processor, a microphone for generating an input signal corresponding to the audio alert and the background noise, and a memory storing processor executable instructions that, when executed by the processor, cause the processor to receive an audio input signal from a microphone, receive a reference signal corresponding to the audio alert, obtain from the audio input signal and the reference signal a background noise estimate and audio alert estimate represented at the microphone, generate an audibility metric representing human perception of the audibility of the audio alert based on a comparison between the background noise estimate and the audio alert estimate, and cause an action to be taken based on the audibility metric.

LL. The system of clause KK, wherein the comparison is a short-time cross correlation comparison.

MM. The system of clause KK or LL, wherein the comparison is based on a signal-to-noise ratio of the audio alert estimate to the background noise estimate.

NN. The system of any one of clauses KK to MM, wherein the process is further configured to generate the audibility metric based on a frequency-weighting that correlates with human perception of relative loudness.

OO. The system of any one of clauses KK to NN, wherein the process is further configured to obtain the audio alert estimate based on an impulse response of an acoustic path between a speaker and the microphone.

PP. The system of any one of clauses KK to OO, wherein the process is further configured to obtain the background noise estimate based on adaptively filtering the audio alert from the input signal using the reference signal.

QQ. The system of any one of clauses KK to PP, wherein the processor is further configured to obtain an background noise estimate based on a comparison between an acoustic power of the input signal when the audio alert is active and an acoustic power of the input signal when the audio alert is inactive.

RR. The system of any one of clauses KK to QQ, wherein the action to be taken is to modify one or more properties of the audio alert and repeat playback.

SS. The system of any one of clauses KK to RR, wherein the action to be taken is to provide visual or haptic feedback to a human.

TT. A non-transitory computer-readable storage medium storing processor-executable instructions to estimate human perception of the audibility of an audio alert in the presence of a background noise, wherein the processor-executable instructions, when executed by a processor, are to cause the processor to receive an audio input signal from a microphone, obtain a reference signal corresponding to the audio alert, obtain from the audio input signal and the reference signal a background noise estimate and audio alert estimate represented at the microphone, generate an audibility metric representing human perception of the audibility of the audio alert based on a comparison between the background noise estimate and the audio alert estimate, and cause an action to be taken based on the audibility metric.

Example embodiments of the present application are not limited to any particular operating system, system architecture, mobile device architecture, server architecture, or computer programming language.

It will be understood that the applications, modules, routines, processes, threads, or other software components implementing the described method/process may be realized using standard computer programming techniques and languages. The present application is not limited to particular processors, computer languages, computer programming conventions, data structures, or other such implementation details. Those skilled in the art will recognize that the described processes may be implemented as a part of computer-executable code stored in volatile or non-volatile memory, as part of an application-specific integrated chip (ASIC), etc.

Certain adaptations and modifications of the described embodiments can be made. Therefore, the above discussed embodiments are considered to be illustrative and not restrictive.

What is claimed is:

1. A method of estimating human perception of the audibility of an audio alert in the presence of a background noise, the method comprising:
   in an alert audibility estimation system,
      obtaining an input signal from a microphone,
      obtaining, from an audio alert generation system for generating the audio alert, a real-time stream including a reference signal corresponding to the audio alert as the audio alert is being generated by the audio alert generation system,
      obtaining from the input signal, using the reference signal, a background noise estimate and audio alert estimate represented at the microphone,
      calculating an audibility metric representing human perception of audibility of the audio alert based on a comparison between the background noise estimate and the audio alert estimate, the comparison including a short-time cross correlation and a frequency-weighting that correlates with human perception of relative loudness; and
      taking an action based on the audibility metric.

2. The method of claim 1, wherein the comparison is based on a signal-to-noise ratio of the audio alert estimate to the background noise estimate.

3. The method of claim 1, wherein obtaining the background noise estimate is based on adaptively filtering the audio alert from the input signal using the reference signal.

4. The method of claim 1, wherein obtaining the background noise estimate is based on a comparison between an acoustic power of the input signal when the audio alert is active and an acoustic power of the input signal when the audio alert is inactive.

5. The method of claim 1, wherein taking an action based on the audibility metric comprises playing the audio alert louder.

6. The method of claim 1, wherein taking an action based on the audibility metric comprises modifying one or more properties of the audio alert and repeating playback.

7. The method of claim 1, wherein taking an action based on the audibility metric comprises providing visual or haptic feedback to a human.

8. The method of claim 1, wherein the audio alert generation system includes a speaker and wherein receiving the real-time stream as the audio alert is being generated by the audio alert generation system includes receiving the real-time stream as the audio alert is being output by the speaker.

9. The method of claim 1, wherein the audio alert estimate is determined by suppressing noise in the audio alert input signal received from the microphone.

10. An alert audibility estimation system for estimating human perception of the audibility of an audio alert in the presence of a background noise, the system comprising:
    a processor;
    a microphone for generating an input signal corresponding to the audio alert and the background noise; and
    a memory storing processor executable instructions that, when executed by the processor, cause the processor to:
       receive an audio input signal from a microphone;
       receive, from an audio alert generation system for generating the audio alert, a real-time stream including a reference signal corresponding to the audio alert as the audio alert is being generated by the audio alert generation system;
       obtain from the audio input signal, using the reference signal, a background noise estimate and audio alert estimate represented at the microphone;
       calculate an audibility metric representing human perception of the audibility of the audio alert based on a comparison between the background noise estimate and the audio alert estimate, the comparison including a short-time cross correlation and a frequency-weighting that correlates with human perception of relative loudness; and
       cause an action to be taken based on the audibility metric.

11. The system of claim 10, wherein the comparison is based on a signal-to-noise ratio of the audio alert estimate to the background noise estimate.

12. The system of claim 10, wherein the process is further configured to obtain the background noise estimate based on adaptively filtering the audio alert from the input signal using the reference signal.

13. The system of claim 10, wherein the processor is further configured to obtain the background noise estimate based on a comparison between an acoustic power of the input signal when the audio alert is active and an acoustic power of the input signal when the audio alert is inactive.

14. The system of claim 10, wherein the action to be taken is to modify one or more properties of the audio alert and repeat playback.

15. The system of claim 10, wherein the action to be taken is to provide visual or haptic feedback to a human.

16. A non-transitory computer-readable storage medium storing processor-executable instructions to estimate human perception of the audibility of an audio alert in the presence of a background noise, wherein the processor-executable instructions, when executed by a processor in an alert audibility estimation system, are to cause the processor to:

receive an audio input signal from a microphone;

obtain, from an audio alert generation system for generating the audio alert, a real-time stream including a reference signal corresponding to the audio alert as the audio alert is being generated by the audio alert generation system;

obtain from the audio input signal, using the reference signal, a background noise estimate and audio alert estimate represented at the microphone;

calculate an audibility metric representing human perception of the audibility of the audio alert based on a comparison between the background noise estimate and the audio alert estimate, the comparison including a short-time cross correlation and a frequency-weighting that correlates with human perception of relative loudness; and cause an action to be taken based on the audibility metric.

\* \* \* \* \*